(12) United States Patent
Leta et al.

(10) Patent No.: US 6,358,894 B1
(45) Date of Patent: *Mar. 19, 2002

(54) MOLYBDENUM-ANTIOXIDANT LUBE OIL COMPOSITIONS

(75) Inventors: Daniel Paul Leta; Jonathan M. McConnachie, both of Flemington; Edward Ira Stiefel, Bridgewater; Charles Frederick Pictroski, Glen Gardner; Kathleen Marie Creegan, Far Hills, all of NJ (US)

(73) Assignee: Infineum USA L.P., Linden, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/969,277

(22) Filed: Nov. 13, 1997

Related U.S. Application Data

(63) Continuation-in-part of application No. 08/766,827, filed on Dec. 13, 1996, now abandoned.

(51) Int. Cl.$^7$ .................... C10M 139/00; C10M 141/12
(52) U.S. Cl. .................. 508/363; 508/364; 508/370; 508/379; 508/445
(58) Field of Search .............................. 508/363, 364, 508/370, 379, 445

(56) References Cited

U.S. PATENT DOCUMENTS

| | | | |
|---|---|---|---|
| 2,951,040 A | 8/1960 | Hugel et al. ............... 252/33.6 |
| 3,419,589 A | 12/1968 | Larson et al. ............... 260/429 |
| 3,840,463 A | 10/1974 | Froeschmann et al. .... 252/42.7 |
| 4,289,635 A | 9/1981 | Schroeck ............... 252/32.7 E |
| 4,456,538 A | 6/1984 | Ripple ................... 252/32.7 E |
| 4,559,152 A | 12/1985 | Schlicht .................. 252/32.7 E |
| 4,705,641 A | 11/1987 | Goldblatt et al. ............. 252/35 |
| 4,730,064 A | 3/1988 | Halbert et al. ................. 556/15 |
| 4,846,983 A | 7/1989 | Ward, Jr. .................... 252/33.6 |
| 4,915,857 A | 4/1990 | Emert et al. ............ 252/32.7 E |
| 4,966,719 A | 10/1990 | Coyle et al. ................ 252/42.7 |
| 4,978,464 A | 12/1990 | Coyle et al. ................ 252/42.7 |
| 4,995,996 A | 2/1991 | Coyle et al. ................ 252/42.7 |
| 5,013,467 A | 5/1991 | Emert et al. ................ 252/46.4 |
| 5,049,290 A | 9/1991 | Emert et al. ............ 252/32.7 E |
| 5,837,657 A | * 11/1998 | Fang et al. |
| 5,888,945 A | * 3/1999 | Stiefel et al. |
| 6,010,987 A | * 1/2000 | Stiefel et al. |

FOREIGN PATENT DOCUMENTS

| | | | |
|---|---|---|---|
| WO | WO95/07963 | 3/1995 | ........ C10M/141/08 |
| WO | WO95/19411 | 7/1995 | ........ C10M/135/18 |

OTHER PUBLICATIONS

Mitchell et al, "Molybdenum Phosphorodithioato Complexes . . . " in Barry & Mitchell, eds., Proceedings of the 4th Climax Int'l. Conference on Chem and Uses of Molybdenum, Ann Arbor, MI, pp. 212–217 (1982).

Meienberger et al, "The reactivity of complexes containing the . . . ", Inorganica Chimica Acta. 213 (1993) pp. 157–169.

Jain et al, "The role of metallic stearate additions in solid lubricants", Wear, 148 (1991), 1–13.

Shibahara, "Synthesis of sulphur–bridged molybdenum and tungsten coordination compounds", Coordination Chemistry Reviews, 123 (1993), 73–147.

* cited by examiner

Primary Examiner—Jerry D. Johnson

(57) ABSTRACT

The invention relates to lubricating oil compositions of a major amount of an oil of lubricating viscosity in admixture with an effective minor amount of an oil soluble or dispersible trinuclear molybdenum containing complex and of an antioxidant, preferably, copper containing antioxidants and diphenyl amines and effective diphenylamine derivatives to enhance the lubricating properties of the oil. Also included are additive concentrates containing these compositions. The invention further includes the method of making these compositions.

34 Claims, 5 Drawing Sheets

MOLYBDENUM-ANTIOXIDANT LUBE OIL COMPOSITIONS

This application is a continuation-in-part of U.S. Ser. No. 08/766,827 filed Dec. 13, 1996 now abandoned.

FIELD OF THE INVENTION

The present invention relates to lubricant compositions containing molybdenum compounds and antioxidants and methods of making them.

BACKGROUND OF THE INVENTION

Molybdenum disulfide is a known lubricant additive. Unfortunately, it has certain known disadvantages some of which are caused by its insolubility in lubricating oils. Therefore, certain oil-soluble molybdenum sulfur-containing compounds have been proposed and investigated as lubricant additives. For example, U.S. Pat. No. 2,951,040 discloses an oil-soluble molybdic xanthate as useful in lubricating compositions. U.S. Pat. No. 3,419,589 discloses the use of certain "sulfurized" molybdenum (VI) dithiocarbamates as lubricant additives. These additives are described as being oil-soluble or at least capable of being easily suspended in oils. U.S. Pat. No. 3,840,463 discloses the use of certain metal dithiocarbamates or dithio-phosphates in combination with metal-free additives that contain sulfur and phosphorus. U.S. Pat. No. 4,966,719, U.S. Pat. No. 4,995,996, and U.S. Pat. No. 4,978,464 all relate to the preparation and use of molybdenum compounds.

U.S. Pat. No. 4,705,641 discloses the use of certain copper salts and molybdenum salts in a basestock as antioxidants and antiwear agents. Copper and molybdenum carboxylates are preferred. The uses or benefits of trinuclear molybdenum containing compounds are not disclosed, and, in fact, oil-soluble trinuclear molybdenum compounds were not known at the time of the invention disclosed in the foregoing patent.

Dinuclear molybdenum compounds known in the art are characterized by a different oxidation state (Mo(V)) from that of trinuclear containing molybdenum compounds (Mo(IV)) of the present invention. Thus, one skilled in the art would not be able to predict the behavior of these Mo(IV) compounds in lubricating oils from the behavior of the dinuclear compounds. More specifically, in view of the difference in oxidation state, the performance of such compounds in redox reactions typical of systems that contain lube oil additives would not be known or predictable given a knowledge of the performance of dinuclear molybdenum compounds in those systems.

U.S. Pat. No. 4,559,152 discloses oil soluble salts of organophosphorus acids prepared by reacting at least one organophosphorus acid in an inert solvent mixed with a polar solvent and an oxymolybdenm compound of certain formulas. However, oxymolybdenum compounds containing trinuclear molybdenum were not synthesized. U.S. Pat. No. 4,559,152 discloses only an elemental analysis of the products, and the ratios of elements disclosed does not, in itself, indicate the presence or teach the preparation of trinuclear oxymolybdenum compounds. In fact, the presence of excess alkyl dithiophosphate ligand reactants as contaminants in the reaction products or a mixture of mono-, di- and tetranuclear oxymolybdenum compounds as products could yield Mo and P ratios identical to those expected for trinuclear oxymolybdenum compounds, without producing them.

U.S. Pat. No. 4,846,983 discloses and claims metal oxygen (and optionally sulfur) core containing compositions in which the core contains at least one generally from 1 to 25 and the metal can be molybdenum. However, oxymolybdenum and oxosulfidomolybdenum compounds containing trinuclear molybdneum were not synthesized. The '983 patent discloses a novel method for generating $H_2S$, through the use of monoalkylthiocarbamates, which decompose upon heating and release $H_2S$. The synthetic conditions in '983 are similar to those disclosed in patents and known in the art to make mononuclear and dinuclear molybdenum thiocarbamates.

Trinuclear molybdenum compounds have been reported but they are either ionic or have ligands with short chain alkyl groups, see, e.g., Shibahara, Coord. Chem. Rev. 123, 73–148 (1993). The reported compounds are consequently not oil soluble, and they have not been reported as lubricating oil additives.

WO 95/07963 to Shaub teaches lubricating compositions of an aromatic amine of a specified formula and dinuclear molybdenum compounds of the general formula $Mo_2O_2S_2(dtc)_2$ and $Mo_2S_4(dtc)_2$ (dtc means dithiocarbamates) have synergistic antioxidant properties. However, Shaub's comparative example indicates that a different molybdenum compound $Mo(S_2)(dtc)_3$, does not exhibit such synergies with aromatic amines. The results indicates that a synergistic effect between any given molybdenum compounds and aromatic amines would not be predictable or expected. EP 94928344.4 discloses the use of diphenylamine antioxidant in combination with molybdenum.

There is a continuing need for additives that demonstrate enhanced lubricating properties, particularly friction reducing and/or anti-wear, and that are compatible with existing additive packages. Applicants' invention addresses these needs.

SUMMARY OF THE INVENTION

Figure 1:
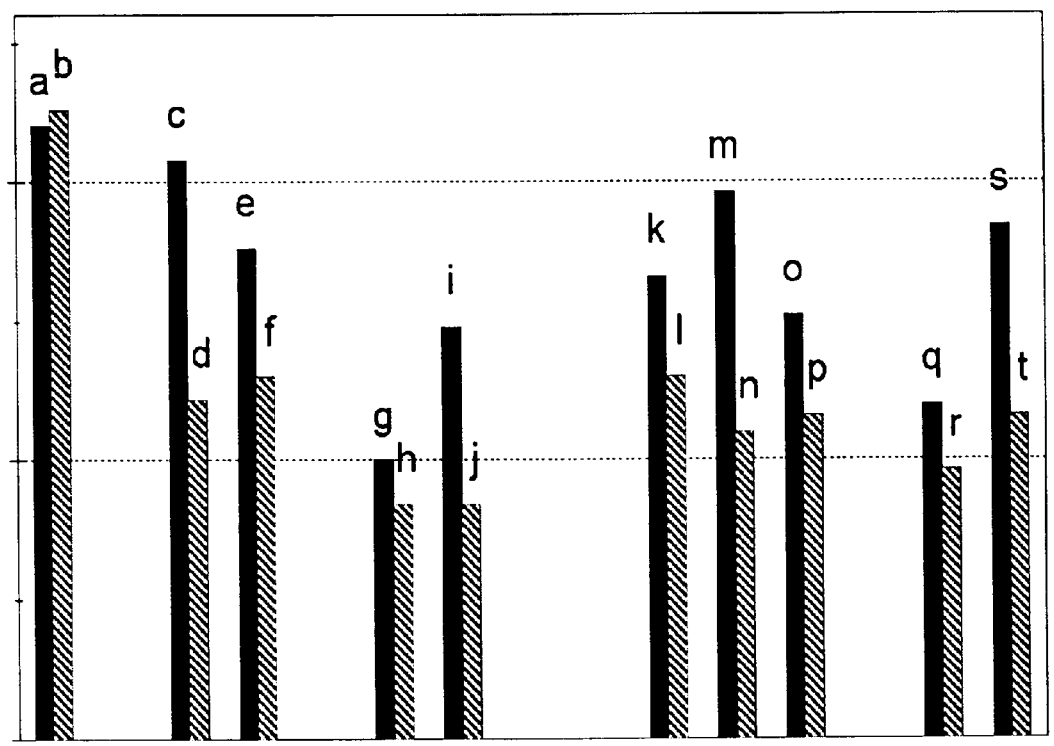
FIG. 1 demonstrates the average friction coefficients obtained from 2 hour Falex block-on-ring testing of molybdenum compounds and molybdenum compounds in an oil formulated with or without antioxidants but without ZDDP. The y-axis is from 0.0 to 0.13.

The present invention provides for lubricating compositions comprising a major amount of an oil of lubricating viscosity and a minor amount of at least one antioxidant and at least one oil soluble trinuclear molybdenum containing compound. Thus the compounds are oil soluble compounds comprising a trinuclear molybdenum core. Preferably the core contains trinuclear molybdenum and sulfur. When the core consists of trinuclear molybdenum and sulfur it is represented by the formula $MO_3S_k$, and the compositions with attached ligands, $L_n$, is represented by the formula $Mo_3S_kL_n$. These are represented by the formulas $MO_3S_kL_n$, and when associated with a neutral electron donating compound, $Q_z$ which is present to fill any vacant coordination sites on the trinuclear molybdenum compound, the formula is $MO_3S_kL_nQ_z$. In the formulas, the L are independently selected ligands, k is at least 4; typically k varies from 4 through 10, more typically 4 through 7, preferably k is 4 or 7, n varies from 1 through 4; Q, the neutral electron donating compound may be any such species known in the art including water, amines, alcohols, phosphines, and ethers, and z ranges from 0 to 5 (z includes nonstoichiometric, i.e., non-integer values). Mixtures are also included. Preferably the trinuclear molybdenum compounds and antioxidants are oil soluble or dispersible. Preferred antioxidants are copper containing antioxidants, and aromatic amine, i.e., amine-containing antioxidants. The ratio of trinuclear molybdenum compound to antioxidant may be varied depending on the particular antioxidant chosen, but in all cases will be an effective amount to enhance the lubricating properties of the oil. Concentrates containing the mixture of trinuclear molybdenum compound and antioxidant are also included.

The present invention also provides for the method of making the lube oil composition and concentrates disclosed herein and described previously.

The present invention also provides for a method for lubricating mechanical engine components particularly an internal combustion engine by adding an oil of lubricating viscosity containing at least one antioxidant and at least one trinuclear molybdenum compound described above thereto.

The present invention may suitably comprise, consist or consist essentially of the elements described herein and includes the products produced by the processes disclosed herein.

The lubricant compositions of this invention have enhanced lubricating properties, particularly antiwear and friction-reducing properties, and also are compatible with other additives used in formulating commercial lubricating compositions. Additional improved antioxidancy of the lubricating oils may be seen.

DETAILED DESCRIPTION OF THE INVENTION

The lubricant compositions of the present invention include a major amount of oil of lubricating viscosity. This oil may be selected from vegetable, animal, mineral, or synthetic oils. The oils may range in viscosity from light distillate mineral oils to heavy lubricating oils such as gas engine oil, mineral lubricating oil, motor vehicle oil, and heavy duty diesel oil. The oils may be unrefined, refined or re-refined.

In general, the viscosity of the oil will range from about 2 centistokes to about 30 centistokes and especially in the range of 5 centistokes to 20 centistokes at 100° C.

Examples of suitable antioxidants are selected from a group consisting of copper containing antioxidants, sulfur-containing antioxidants, aromatic amine containing antioxidants and phenolic antioxidants.

Examples of suitable copper-containing antioxidants include oil soluble copper compounds mentioned in published European Patent Application Nos. 24 146 B, 280 579 A and 280 580 A, the disclosures of all of which are incorporated herein by reference. Thus, for example, the copper may be blended into the oil as an oil-soluble copper salt of a synthetic or natural carboxylic acid. Examples of carboxylic acids from which suitable copper salts may be derived include $C_2$ to $C_{18}$ fatty acids (e.g., acetic acid, stearic acid and palmitic acid), unsaturated acids (e.g., oleic acid), branched carboxylic acids (e.g., naphthenic acids of molecular weight of from 200 to 500, neodecanoic acid and 2-ethylhexanoic acid), and alkyl-or alkenyl-substituted dicarboxylic acids (e.g., polyalkenyl-substituted succinic acids such as octadecenyl succinic acids, dodecenyl succinic acids and polyisobutenyl succinic acids). In some cases, suitable compounds may be derived from an acid anhydride, for example, from a substituted succinic anhydride. The copper antioxidant may be, for example, a copper dithiocarbamate or copper dithiophosphate. Other copper and sulfur- containing antioxidant compounds, for example, copper mercaptides, xanthates, thioxanthates, are also suitable for use in accordance with the invention, as are copper sulfonates, phenates (optionally sulfurized) and acetylacetonates. Other copper compounds which may be used in accordance with the invention are overbased copper compounds. Examples of such compounds, and of processes for their preparation, are given in U.S. Pat. No. 4,664,822 and European Specification No. 0 425 367 A, the disclosures of both of which are incorporated herein by reference. The copper compound may be in cuprous or cupric form.

Examples of suitable aromatic amine-containing antioxidants are aromatic amines which have at least one aromatic group directly attached to at least one amine nitrogen atom. Secondary aromatic amines, especially those having two aromatic groups attached to the same amine nitrogen atom, are preferred, but the use of other aromatic amines is not excluded. The aromatic groups advantageously contain from 6 to 16 carbon atoms. The amines may contain one or more aromatic groups, for example at least two aromatic groups. Where there are two aromatic groups both are preferably bonded directly to the same amine nitrogen. Compounds in which two aromatic groups are linked by a covalent bond or by an atom or group (e.g., an oxygen or sulfur atom, or a —CO—, —$SO_2$— or alkylene group) may be used. Aromatic rings, which are preferably aromatic hydrocarbon rings may be unsubstituted or substituted by one or more substituents selected from alkyl, cycloalkyl, alkoxy, aryloxy, acyl, acylamino, hydroxy, and nitro groups. Amines containing alkyl-substituted aromatic hydrocarbon rings are preferred, especially those containing two alkyl-substituted phenyl groups. Preferred N-aryl amines for use in accordance with the invention are naphthylamines and, especially, diphenylamines, including alkyl substituted diphenylamines, wherein the alkyl group may be the same or different, having 1 to 28 carbon atoms. Other nitrogen containing antioxidants, for example, phenothiazine type compounds, may also be used in this invention.

Examples of phenolic antioxidants include (a) sterically hindered tertiary-alkylated monohydric phenols such as those described in more detail in U.S. Pat. Nos. 2,944,086; 3,043,775; and 3,211,652; and (b) methylene-bridged tertiary alkyl polyphenois, such as 4,4'-methylene bis (2,6-di-tert-butylphenol) and 2,2'-methyl bis (4,6-di-(1,1,2-trimethylpropyl)phenol), and mixtures of (a) and (b) such as those described in more detail in EP 0456925 B1.

Examples of sulfur-containing antioxidants (compounds) are alkaline earth metal salts of alkylphenolthioesters having preferably $C_5$ to $C_{12}$ alkyl side chains, calcium nonylphenol sulfide, ashless oil soluble phenates and sulfurized phenates, phosphosulfurized or sulfurized hydrocarbons, phosphorus esters and other molybdenum containing compounds. Other examples of sulfur containing antioxidants are metal salts of dihydrocarbyl dithiophosphate or dihydrocarby dithiocarbamate compounds, wherein the metal is selected from Zn, Mn, Ni, Al, Group metals and Group II metals. Other sulfur containing compounds include those described in EP 699 759 A2, for example, sulfides of oils, fats or polyolefins, in which a sulfur atom group having two or more sulfur atoms is adjoined and bonded together in a molecular structure. Examples include sulfurized sperm oil, sulfurized pinene oil, sulfurized soybean oil, sulfurized polyolefin, sulfurized esters, dialkyl disulfide, dialkyl polysulfide, dibenzyl disulfide, ditertiary butyl disulfide, polyolefin polysulfide, thiadiazol type compound such as bis-alkyl polysulfanyl thiadiazole, and sulfurized phenol.

Preferable antioxidants are copper-containing antioxidants, aromatic amine containing compounds including diphenylamines and (derivatives thereof that have an effect herein comparable to diphenylamines), and mixtures thereof. Examples of copper containing antioxidants include copper polyisobutylene succinic anhydride ("copper PIBSA") and copper oleate; diphenylamines include all effective derivatives of diphenylamines.

The lubricant compositions of the present invention also include a minor amount of at least one antioxidant and at least one oil soluble trinuclear molybdenum compound. Thus the compositions are oil soluble compounds comprising a trinuclear molybdenum core. Preferably, they comprise a trinuclear molybdenum sulfur core. The trinuclear molybdenum compounds having sulfur containing cores are of the formula $MO_3S_kL_n$ and as associated with an electron donating compound $Q_z$, the formula is $MO_3S_kL_nQ_z$ and mixtures thereof. The lubricant composition may include a mixture of the trinuclear molybdenum compounds and antioxidants of the types disclosed herein, the lubricating oil and/or other additives disclosed herein per se, and/or of any intermediates and reaction products occurring as a result of the mixture. In combination, the antioxidants and trinuclear molybdenum compounds are present in a minor effective amount to produce the enhanced lubricating performance, particularly friction reduction and/or antiwear properties in the oil.

The trinuclear molybdenum compounds disclosed herein in combination with the foregoing antioxidants produce an enhanced effect with respect to lubricating performance not evident in the presence of the trinuclear molybdenum compounds or antioxidants alone. Additionally, the enhanced effect of the trinuclear molybdenum compounds in the presence of these antioxidants would not be expected by one skilled in the art based on the performance of dinuclear molybdenum and copper additives due to the difference in oxidation state of the molybdenum in the trinuclear molybdenum compounds and the dinuclear molybdenum compounds. The $MO_3S_k$ cores have a net charge of +4. Consequently, in order to neutalize such cores, the total charge among all ligands, L, in the $MO_3S_kL_n$, must be −4. Four L monoanionic ligands are preferred. It is believed that oxygen and/or selenium may be substituted for sulfur in the core. However, in addition to the trinuclear molybdenum the core should contain at least one, and preferably be primarily (i.e., greater than 50%) sulfur. Most preferred is a core consisting of molybdenum and sulfur alone. The balance, if any, is oxygen and/or selenium. Trinuclear $MO_3S_k$ cores of this type have not been used in lube oil compositions prior to the present invention.

When the core consists only of trinuclear molybdenum and sulfur it is represented by the formula $MO_3S_k$, and with ligands attached is represented by the formula $MO_3S_kL_n$.

The electron donating compound, $Q_z$, is merely present in the preceding formulas to fill any vacant coordination sites on the trinuclear molybdenum compound, as previously discussed.

When the core contains trinuclear molybdenum, sulfur and oxygen or selenium, it is represented by the formula $MO_3S_kE_xL_n$ and $MO_3S_kE_xL_nQ_z$ wherein E is selected from oxygen and selenium and the sum of x and k is at least 4.

In all the formulas, $L_n$ are independently selected ligands and render the compound oil soluble, k is at least 4, and typically k varies from 4 through 10 more typically 4 through 7, preferably 4 or 7, n varies from 1 to 4, $Q_z$ is any neutral electron donating compounds as known to those skilled in the art, including water, amines, alcohols, phosphines, and ethers, and z ranges from 0 to 5. The ligands are independently selected from the group of:

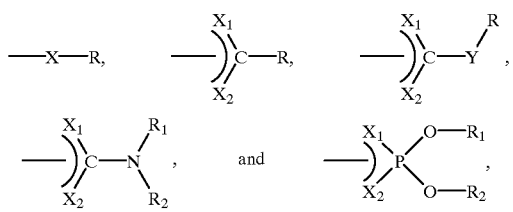

and mixtures thereof, and perthio derivatives thereof wherein X, $X_1$, $X_2$, and Y are independently selected from the group of oxygen and sulfur, and wherein $R_1$, $R_2$, and R are independently selected from the group consisting of H and organo groups that may be the same or different. Preferably the organo groups are hydrocarbyl groups such as alkyl (e.g., in which the carbon atom attached to the remainder of the ligand is primary, secondary or tertiary), aryl, substituted aryl and ether groups. More preferably, each ligand has the same hydrocarbyl group.

Importantly, the organo groups of the ligands have a sufficient number of carbon atoms to render the trinuclear molybdenum compound soluble or dispersible in the oil. The compounds' oil solubility or dispersibility may be influenced by the number of carbon atoms in the ligands. Preferably the ligand source chosen has a sufficient number of carbon atoms to render the compound soluble or dispersible in the oil. In the compounds in the present invention, the total number of carbon atoms present among all of the organo groups of the compounds' ligands typically will be at least 21, such as at least 25, at least 30 or at least 35. For example, the number of carbon atoms in each alkyl group will generally range between about 1 to 100, preferably 1 to 30 and more preferably between 4 to 20. Preferred ligands include dialkyldithiophosphate ("ddp"), xanthates, thioxanthates, and dialkyldithiocarbamate ("dtc"), and of these the dtc is more preferred.

Multidentate organic ligands containing at least two of the above functionalities are also capable of binding to at least one of the trinuclear cores and serving as ligands. Without wishing to be bound by any theory, it is believed that one or more trinuclear molybdenum cores may be bound or interconnected by means of at least one of these multidentate ligands. Such structures fall within the scope of this invention. This includes the case of a multidentate ligand having multiple connections to one core.

Those skilled in the art will realize that formation of the compounds will require selection of appropriate ligands having suitable charge to balance the corresponding core's charge.

The term "hydrocarbyl" denotes a substituent having carbon atoms directly attached to the remainder of the ligand and is predominantly hydrocarbyl in character within the context of this invention. Such substituents include the following: (1) hydrocarbon substituents, that is, aliphatic (for example alkyl or alkenyl), alicyclic (for example cycloalkyl or cycloalkenyl) substituents, aromatic-, aliphatic-and alicyclic-substituted aromatic nuclei and the like, as well as cyclic substituents wherein the ring is completed through another portion of the ligand (that is, any two indicated substituents may together form an alicyclic group); (2) substituted hydrocarbon substituents, that is, those containing non-hydrocarbon groups which, in the context of this invention, do not alter the predominantly hydrocarbyl character of the substituent. Those skilled in the art will be aware of suitable groups (e.g., halo, (especially chloro and fluoro), amino, alkoxyl, mercapto, alkylmercapto, nitro, nitroso, sulfoxy, etc.); (3) hetero substituents, that is, substituents which, while predominantly hydrocarbon in character within the context of this invention, contain atoms other than carbon present in a chain or ring otherwise composed of carbon atoms.

Generally, the trinuclear molybdenum containing compounds can be prepared by combining a liquid containing a suitable molybdenum source, a ligand source and, optionally, a sulfur abstracting agent. The appropriate liquid/solvent may, for example, be aqueous or organic. Oil-soluble or dispersible trinuclear molybdenum compounds can be prepared by reacting in the appropriate solvent(s) $(NH_4)_2Mo_3S_{13} \cdot n(H_2O)$, wherein n varies between 0 and 2 and includes non-stoichiometric values, with a suitable ligand source such as a tetralkylthiuram disulfide. Other oil-soluble trinuclear molybdenum compounds can be formed during a reaction in the appropriate solvent(s) of $(NH_4)_2Mo_3S_{13} \cdot n(H_2O)$, wherein n varies between 0 and 2 and includes non-stoichiometric values, a ligand source such as tetralkylthiuram disulfide, dialkyldithiocarbamate, or dialkyldithiophosphate, and a sulfur abstracting agent such as cyanide ions, sulfite ions, or substituted phosphines. Alternatively, a trinuclear molybdenum-sulfur halide salt such as $[M']_2[Mo_3S_7A_6]$, wherein M' is a counter ion, and A=Cl, Br, or I, may be reacted with a ligand source such as a dialkyldithiocarbamate or dialkyldithiophosphate in the appropriate solvent(s) to form an oil-soluble or dispersible trinuclear molybdenum compound. The trinuclear molybdenum compounds are related by the number of sulfur atoms in the molybdenum core. Within the disclosed range, the number of the sulfur atoms in the core may be altered by the addition of sulfur abstractors such as cyanide and substituted phosphines or sulfur donators such as elemental sulfur and organic trisulfides to the trinuclear molybdenum compounds.

In general, the trinuclear molybdenum compounds can be purified by well known techniques such as chromatography and the like; however, it is not necessary to purify the compounds.

The admixture of antioxidants with the trinuclear molybdenum compounds allows reduction in molybdenum treat rates for effective friction reduction. The benefits are exemplified herein with bis-alkyldiphenyl amine ("DPA") and copper-polyisobutylene succinic anhydride, with copper-PIBSA demonstrating a stronger enhancement. Thus in the present invention, the combination of the trinuclear molybdenum compounds and the antioxidants demonstrates enhanced performance at reduced treat rates than dinuclear molybdenum additives such as $Mo_2O_2S_2(dtc)_2$. The enhanced performance of the combination of the trinuclear molybdenum compounds with these antioxidants typically can allow the use of the trinuclear molybdenum compounds at concentrations about two times lower than without the antioxidants.

Effective enhancement of lubricating performance, e.g., friction reduction (decreased friction coefficients), can be achieved according to the present invention. The lubricating compositions contain minor effective amounts, preferably ranging from 1 to 2000 ppm molybdenum from the trinuclear molybdenum compounds, preferably 5–750 ppm, more preferably 10–300 ppm all based on the weight of the lubricating composition. The amount of antioxidant additive is a minor effective amount, preferably from about 0.001 to about 10 wt % based on the weight of the finished oil, more preferably, from about 0.01 to about 2 wt % of the weight of the finished oil. Typically for copper containing antioxidants the amount is 1 to 1000 ppm of copper, 1 to 200 ppm copper, and for antioxidants, e.g., aromatic amine and sulfur containing, phenolic and ZDDP antioxidants containing antioxidants the preferred amount is up to 2 wt %. Within the above ranges one skilled in the art can select the particular effective combinations of amounts to produce the enhancement in lubricating properties, particularly friction reducing and/or anti-wear, desired for the particular application. The selection within these ranges may be accomplished to optimize for either enhanced friction reducing or anti-wear performance or both.

The effective amount of trinuclear molybdenum compound (with or without antioxidants), should not exceed the optimal concentration beyond which friction coefficients may increase.

Thus the trinuclear molybdenum compounds allow for the use of a decreased amount of antioxidant or, alternatively, with an equal amount of antioxidant they allow for the use of a decreased amount of trinuclear compound as compared to the use of dinuclear molybdenum compounds, while still achieving the desired enhanced lubricating, i.e., wear and/or friction, performance in the oil, thus making their use potentially more cost effective than current additives.

These benefits can be achieved in basestock as well as fully formulated lube oils. Essentially phosphorus and/or sulfur-free oils also may also be treated.

The lubricating oil compositions of the present invention may be prepared by adding to an oil of lubricating viscosity a mixture of an effective minor amount of at least one trinuclear molybdenum compound, which may be prepared in amounts as described previously, and at least one previously-described antioxidant. This preparation may be accomplished by adding the trinuclear molybdenum compound directly to the oil or by first mixing the trinuclear molybdenum compound in a suitable carrier fluid to achieve oil solubility or dispersibility, and adding the mixture to the lubricating oil. The antioxidant may be added to the oil by any method known to those skilled in the art, either prior to, contemporaneously with, or subsequent to addition of the trinuclear molybdenum compound.

The terms "oil-soluble" or "dispersible" used herein do not necessarily indicate that the compounds or additives are soluble, dissolvable, miscible, or capable of being suspended in the oil in all proportions. These do mean, however, that they are, for instance, soluble or stably dispersible in oil to an extent sufficient to exert their intended effect in the environment in which the oil is employed. Moreover, the additional incorporation of other additives may also permit incorporation of higher levels of a particular additive, if desired.

Concentrates of the trinuclear molybdenum compounds and antioxidants in a suitable oleagenous, typically hydrocarbon, carrier fluid provide a convenient means of handling them before their use. Oils of lubricating viscosity, such as those described above as well as aliphatic, naphthenic, and aromatic hydrocarbons are examples of suitable carriers for concentrates. These concentrates may contain about 1 to about 90 wt % of the trinuclear molybdenum compound and antioxidant based on the weight of the concentrate, preferred is 1 to 70 wt %, more preferably 20 to 70 wt %.

The lubricating oil compositions made by combining an oil of lubricating viscosity containing at least one antioxidant of the types and in the amounts described herein and at least one trinuclear molybdenum compound of the types and in the amounts described herein may be used to lubricate mechanical engine components, particularly an internal combustion engine, by adding the lubricating oil thereto.

Other known lubricant additives also may be used for blending in the lubricant composition of this invention. These include dispersants, detergents, e.g., single or mixed metal detergent systems, pour point depressants, viscosity improvers, antioxidants, surfactants, antiwear agents, and friction reducing agents. These can be combined in proportions known in the art. For example, additives containing phosphorus and/or sulfur compounds such as ZDDP can be prepared and used with the compounds of the present invention. However, the compounds of the present invention may be effective or may even possess improved properties when used in lubricating compositions that are free or substantially free of added phosphorus and/or sulfur, i.e., phosphorus and/or sulfur in addition to (i.e., except for) the phosphorus or sulfur contained in the trinuclear molybdenum compounds themselves. A lubricating composition that is substantially free of phosphorus and/or sulfur is one in which the amount of phosphorus and/or sulfur is not more than is inherently present in base oils of lubricating viscosity.

The invention will be more fully understood by reference to the following examples.

General

As used herein "coco" is an alkyl chain or mixture of chains of varying even numbers of carbon atoms of from about typically $C_8$ to $C_{18}$, "dtc" means dialkyldithiocarbamate, "ddp" means dialkyldithiophosphate.

The procedures and equipment used for the Falex Block-On-Ring test were similar to those used in ASTM677-83 (Ranking Resistance of Materials to Sliding Wear Using Block-On-Ring Wear Test).

As used herein "AO" means antioxidant, "eh" means "ethylhexyl". SL300™ and SL321™ are commercial dinuclear molybdenum compounds available from Ashai Denka, Japan. MV-L™ is Moly Van-L a commercial dinuclear molybdenum compound available from Vanderbilt Chemical Company.

EXAMPLE 1

The mixtures were prepared as follows:

The dinuclear molybdenum complex or trinuclear molybdenum containing compound was placed with the appropriate equivalent of Cu(II) carboxylate (2.0 equivalents for $Mo_2S_4(dtc)_2$; 0.5, 1.0, and 1.5 equivalents for $Mo_3S_4(dtc)_4$ or $Mo_3S_4(ddp)_4$) in a flask and tetrahydrofuran ("THF") is added. After sting for 24 hours the THF was pumped off and the resulting mixture dissolved in S150N base oil with zinc dialkyl dithiophosphate ("ZDDP"). Alternatively, the examples indicated with and asterisk (*) were prepared by mixing the additives in S150N with ZDDP at temperatures up to 70° C. for a period of time sufficient to dissolve the additives. The friction and wear results are detailed in Table 1 below. The compositions formed by the foregoing methods using an $Mo_3$-containing starting material as a class possess UV and IR spectra characteristic of trinuclear molybdenum containing compounds.

Friction and wear testing:

Results of friction and wear tests using the combination of copper and trinuclear molybdenum compounds in S150N with 1% ZDDP are given in Table 1. For comparison purposes the results for the molybdenum in the form of dinuclear $Mo_2S_4(coco_2dtc)_2$, and trinuclear $Mo_3S_4$ $(octyl_2dtc)_2$ or $Mo_3S_4(2-ethylhexyl_2dtc)_2$, $Mo_3S_7$ $(coco_2dtc)_4$ $Mo_3S_4(n-octyl_2ddp)_2$ or $Mo_3S_4(2-ethylhexyl_2ddp)_2$, $Mo_3S_7(lauryl_2ddp)_4$, $Cu(oleate)_2$, and the copper in combination with certain dinuclear and trinuclear molybdenum compounds are listed. Friction and wear data were acquired using a Falex block-on-ring tribometer on sets of S150N with 1% ZDDP with various molybdenum containing compounds at 500 ppm molybdenum concentration. The data was obtained at 420 rpm, load of 220 lb. (100 kg), and a temperature of 100° C. for 2 h. Data reported include the block wear scar volume, measured by profilometry, the end of test friction coefficient ("End Coef."), and the average friction coefficient ("Avg. Coef.") obtained over the 2 hour test. The end of test friction coefficient is indicative of the friction obtained at the conclusion of the test, and the average friction coefficient provides information on the activity of the added material, i.e., samples that attain the same decreased friction coefficients faster are considered to contain more active, friction-reducing compounds.

TABLE 1

Molybdenum at 500 ppm Mo

| Sample | Wear Volume ($10^{-2}$ mm$^3$) | End Coefficient | Average Coefficient |
|---|---|---|---|
| (*) S150N + 1% ZDDP | 1.06 | 0.111 | 0.112 |
| S150N + 1% ZDDP with: | | | |
| (*) 55 ppm Cu as Cu(oleate)$_2$ | 0.46 | 0.108 | 0.108 |
| (*) 110 ppm Cu as Cu(oleate)$_2$ | 0.85 | 0.106 | 0.107 |
| (*) 165 ppm Cu as Cu(oleate)$_2$ | 1.03 | 0.107 | 0.107 |
| Mo$_2$S$_4$(coco$_2$dtc)$_2$ | 1.10 | 0.041 | 0.054 |
| Mo$_2$S$_4$(coco$_2$dtc)$_2$ + 331 ppm Cu as Cu(oleate)$_2$ | 0.54 | 0.041 | 0.048 |
| Mo$_3$S$_4$(octyl$_2$dtc)$_4$ | 1.69 | 0.041 | 0.057 |
| Mo$_3$S$_4$(octyl$_2$dtc)$_4$ + 55 ppm Cu as Cu(oleate)$_2$ | 1.27 | 0.038 | 0.048 |
| Mo$_3$S$_4$(octyl$_2$dtc)$_4$ + 110 ppm Cu as Cu(oleate)$_2$ | 0.64 | 0.038 | 0.047 |
| Mo$_3$S$_4$(octyl$_2$dtc)$_4$ + 165 ppm Cu as Cu(oleate)$_2$ | 0.53 | 0.039 | 0.048 |
| (*) Mo$_3$S$_7$(coco$_2$dtc)$_4$ | 0.62 | 0.044 | 0.058 |
| (*) Mo$_3$S$_7$(coco$_2$dtc)$_4$ + 110 ppm Cu as Cu(oleate)$_2$ | 0.58 | 0.045 | 0.053 |
| Mo$_3$S$_4$(octyl$_2$ddp)$_4$ | 1.64 | 0.040 | 0.060 |
| Mo$_3$S$_4$(octyl$_2$ddp)$_4$ + 55 ppm Cu as Cu(oleate)$_2$ | 1.03 | 0.042 | 0.054 |
| Mo$_3$S$_4$(octyl$_2$ddp)$_4$ + 110 ppm Cu as Cu(oleate)$_2$ | 0.53 | 0.036 | 0.045 |
| Mo$_3$S$_4$(octyl$_2$ddp)$_4$ + 165 ppm Cu as Cu(oleate)$_2$ | 0.43 | 0.038 | 0.048 |
| (*) Mo$_3$S$_7$(lauryl$_2$ddp)$_4$ | 0.49 | 0.037 | 0.049 |
| (*) Mo$_3$S$_7$(lauryl$_2$ddp)$_4$ + 110 ppm Cu as Cu(oleate)$_2$ | 0.36 | 0.034 | 0.044 |

The wear and friction results indicated that a trinuclear molybdenum compound in combination with copper carboxylates had enhanced effect on anti-wear in S150N with ZDDP. The total wear was 50% less than S150N with ZDDP alone and up to 75% less than the trinuclear molybdenum compounds alone in S150N with ZDDP. The trinuclear molybdenum in combination with copper carboxylates also exhibited a tendency toward decreased friction. The examples given for the dinuclear molybdenum ($Mo_2$) complexes demonstrated that significantly more copper was required to obtain performance comparable to trinuclear molybdenum compounds used with lower copper concentrations. Thus, the addition of the trinuclear molybdenum compounds and copper(II) carboxylates to lubricating oils is demonstrated to enhance the lubricating properties of the oils.

EXAMPLE 2

To test the performance of trinuclear molybdenum compounds having dtc and ddp ligands in combination with antioxidants, bench tribometer testing was performed using a Falex Block-On-Ring tribometer. The molybdenum containing compounds were added at a concentration of 500 ppm Mo to an oil which was fully formulated but without ZDDP or supplemental antioxidants. The compounds were also tested in the same no-ZDDP formulation to which two antioxidants, bis-nonyl-diphenylamine (DPA) at 0.35 wt % and copper-polyisobutylene succinic anhydride at 0.4 wt %, yielding approximately 70 ppm copper, were added.

The formulations were tested in a Falex Block-on-Ring (BOR) tribometer at 100° C. with a 220 lb. (100 kg) load, a speed of 420 rpm (44 radians/sec.), and a 2 hour test length. Friction coefficients are reported as both the end of run value and the average value over the entire 2 hours. Data reported included the block wear scar volume, measured by profilometry, the end of test friction coefficient, and the average friction coefficient obtained over the 2 hour test. The end of test friction coefficient is that friction coefficient determined at the end of the test period, and the average friction coefficient provides information on the activity of the added material, i.e., samples that attain the same low friction coefficients faster are considered to contain more active compounds. Results are specified in Table 2.

EXAMPLE 3

A series of oils was prepared using the trinuclear molybdenum compound $MO_3S_4((2\text{-ethylhexyl})_2dtc)_4$. The trinuclear molybdenum compound was prepared in four formulated oils at 150 ppm Mo concentrations.

The frictional performance of the various oils tested was determined using a Cameron-Plint TE77 tribometer. The test protocol used a 6 mm. steel ball in reciprocating motion against a flat steel plate under a normal load of 5 kg., a stroke length of 7 mm., and a reciprocation frequency of 22 Hz. During the test the oil was held for approximately 20 minutes at each of four temperatures 50, 80, 110, and 135° C. while the friction coefficient was measured.

The four formulated, ZDDP-containing base case oils differed only in the presence or absence of various antioxidants. The base case oils are identified in FIGS. 2–5 as:
Case Description
1. base case oil, contains no dialkyldiphenylamine or Cu-polyisobutylene
2. contains dialkyldiphenylamine (0.35%)
3. contains Cu-polyisobutylene succinic anhydride (0.40%)
4. base case oil plus both dialkyldiphenylamine (0.35%) and Cu-polyisobutylene succinic anhydride(0.40%)

Figure 2:
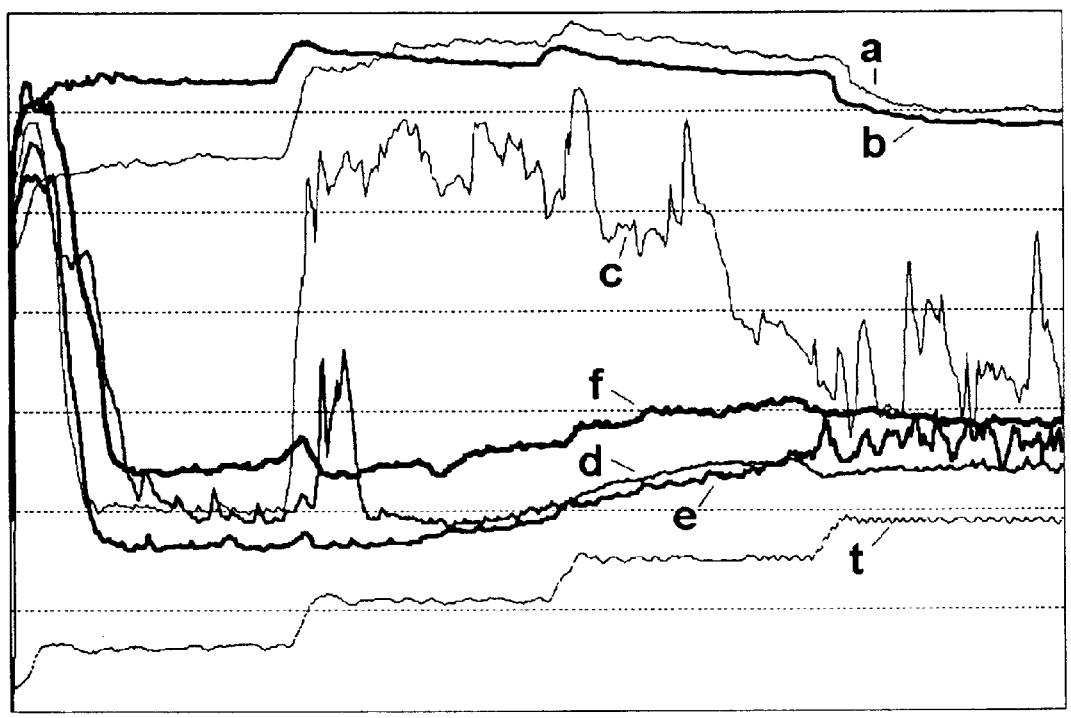
FIG. 2 shows the friction traces for the 'no-molybdenum' base case oils 1 (no antioxidants) and 4 (with both bis-nonyl diphenylamine and Cu-PIBSA), and the friction traces at 150 ppm Mo as $Mo_3S_4((2\text{-ethylhexyl})_2dtc)_4$ in the four base oils.

The friction traces for the 'no-molybdenum' base cases 1 and 4 oils (no antioxidants and both antioxidants) and the friction traces at 150 ppm Mo as $Mo_3S_4((2\text{-ethylhexyl})_2dtc)_4$ in the four base case oils are shown in FIG. 2.

Either with or without the specified antioxidants the friction coefficients are similar and vary between 0.12 and 0.14 throughout the temperature range tested for the no-molybdenum base cases.

At the 150 ppm molybdenum concentration level enhancement in friction coefficients seen for the combination of $Mo_3S_4((2\text{-ethylhexyl})_2dtc)_4$ with the antioxidants, used individually or together.

For comparison purposes a dinuclear Mo compound will be represented by $Mo_2O_2S_2(coco_2dtc)_2$ (MV822 from

TABLE 2

| | Without AO's | | | With AO's | | |
|---|---|---|---|---|---|---|
| Sample | Wear Volume | End Friction Coefficient | Average Friction Coefficient | Wear Volume | End Friction Coefficient | Average Friction Coefficient |
| No ZDDP Base | 1.02 | 0.110 | 0.110 | 1.81 | 0.112 | 0.113 |
| $Mo_2O_2S_2(coco_2dtc)_2$ | 1.83 | 0.108 | 0.104 | 1.48 | 0.053 | 0.061 |
| $Mo_2O_2S_2(2\text{-eh}_2dtc)_2$ | 1.72 | 0.094 | 0.088 | 1.43 | 0.051 | 0.065 |
| $Mo_3S_4(2\text{-eh}_2dtc)_4$ | 1.21 | 0.040 | 0.050 | 1.01 | 0.036 | 0.042 |
| $Mo_3S_7(coco_2dtc)_4$ | 0.91 | 0.039 | 0.074 | 0.92 | 0.033 | 0.042 |
| $Mo_2O_2S_2(2\text{-eh}_2ddp)_2$ (SL-300) | 2.05 | 0.091 | 0.083 | 1.81 | 0.060 | 0.065 |
| $Mo_2O_2S_2(hexyl_2ddp)_2$ (SL-321) | 1.30 | 0.104 | 0.098 | 1.92 | 0.049 | 0.055 |
| $Mo_2O_2S_2(2\text{-eh}_2ddp)_2$ (MV-L) | 2.06 | 0.078 | 0.076 | 1.81 | 0.051 | 0.058 |
| $Mo_3S_4(octyl_2ddp)_4$ | 1.12 | 0.071 | 0.060 | 1.14 | 0.044 | 0.048 |
| $Mo_3S_7(lauryl_2ddp)_4$ | 1.42 | 0.106 | 0.092 | 1.29 | 0.064 | 0.058 |

FIG. 1 demonstrates the average friction coefficients obtained both without and with antioxidants in a no-ZDDP formulation.

The data demonstrate that the trinuclear molybdenum compounds with antioxidants provide enhanced performance, particularly as demonstrated by the average friction coefficients as compared to the dinuclear molybdenum complexes in the presence of antioxidants.

Figure 3:
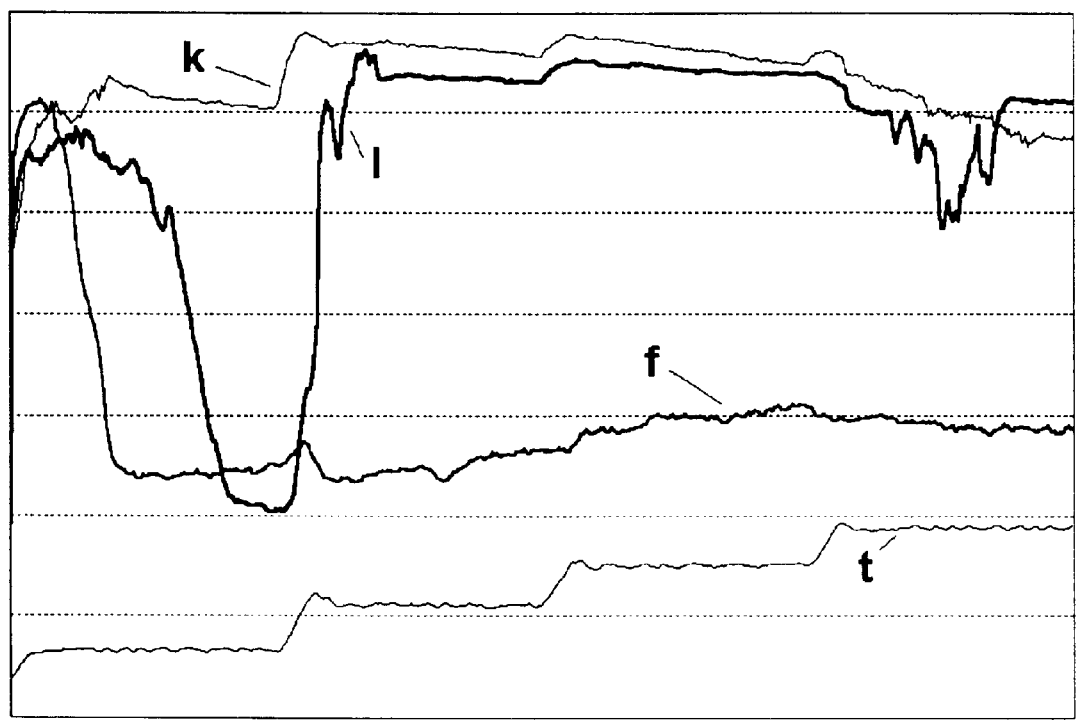
FIG. 3 shows the friction traces for a dinuclear Mo complex, $Mo_2O_2S_2(coco_2dtc)_2$ tested at 150 ppm Mo concentration in oils 1 (no anti-oxidants) and 4 (with both bis-nonyldiphenylamine and Cu-PIBSA), and that of 150 ppm Mo as $Mo_3S_4((2\text{-ethylhexyl})_2dtc)_4$ in oil 4 (both bis-nonyldiphenyl-amine and Cu-PIBSA).

Vanderbilt Chemical Company) was also tested at 150 ppm Mo concentration in oils Case 1 (no antioxidants) and Case 4 (with both dialkyldiphenylamine and Cu-PIBSA). Their friction traces, along with that of 150 ppm Mo as $Mo_3S_4((2\text{-ethylhexyl})_2dtc)_4$ in the Case 4 oil (both antioxidants) are shown in FIG. 3.

The data demonstrate the enhanced performance of the trinuclear molybdenum compounds with antioxidants in comparison to the dinuclear molybdenum compounds at this low concentration of molybdenum.

Example 4

A series of four oils was prepared using the trinuclear molybdenum compound $Mo_3S_7((coco)_2dtc)_4$, at a concentration of 75 ppm Mo.

The frictional performance of the oils was determined using a Cameron-Plint TE77 tribometer. The test protocol used a 6 mm. steel ball in reciprocating motion against a flat steel plate under a normal load of 5 kg., a stroke length of 7 mm., and a reciprocation frequency of 22 Hz. During the test the oil was held for approximately 20 minutes at each of four temperatures 50, 80, 110, and 135° C. while the friction coefficient was measured.

The four base case oils are the same as described in Example 3. The friction traces for the no-molybdenum base case oils, Case 1 and Case 4 (no antioxidants, and both antioxidants) are found in FIG. 2.

Figure 4:
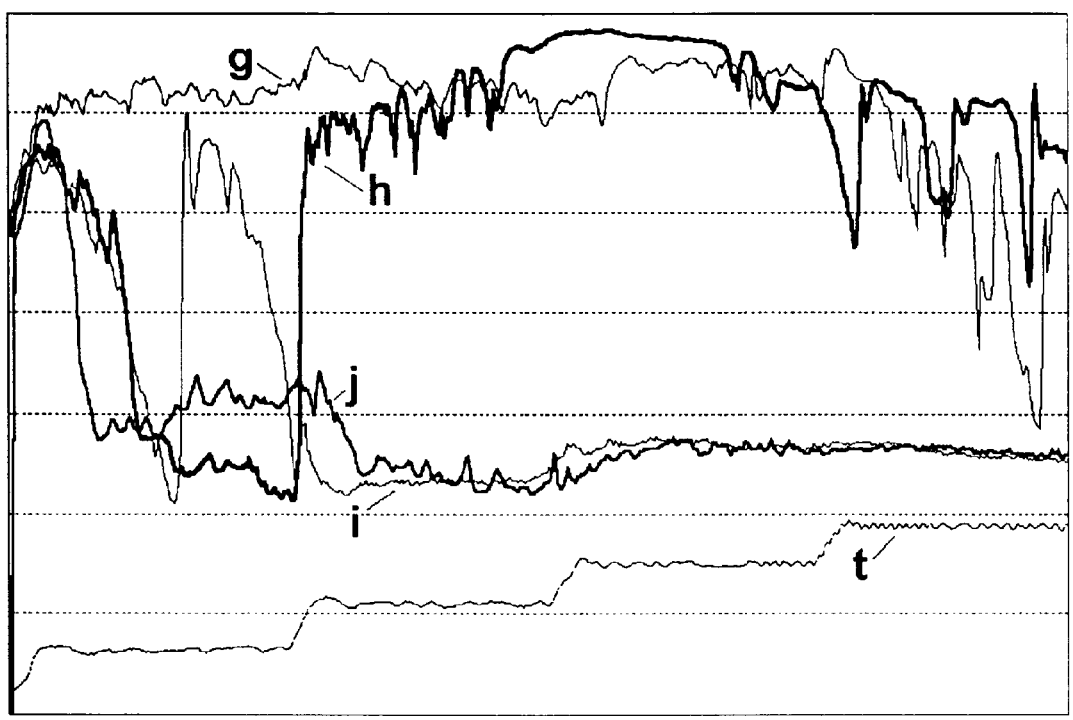
FIG. 4 shows the friction traces for 75 ppm Mo as $Mo_3S_7((coco)_2dtc)_4$ in four base oils.

The friction results for 75 ppm Mo as $Mo_3S_7((coco)_2dtc)_4$ in the four base case oils is shown in FIG. 4.

The data demonstrate that at 75 ppm, only minor frictional improvements over the no-molybdenum base case oils are seen without antioxidants or with the co-addition of diphenylaamine whereas the use of Cu-PIBSA and the combination of Cu-PIBSA and bis(nonyl)diphenylamine yielded enhanced friction coefficients at low concentration of the trinuclear molybdenum compounds.

Figure 5:
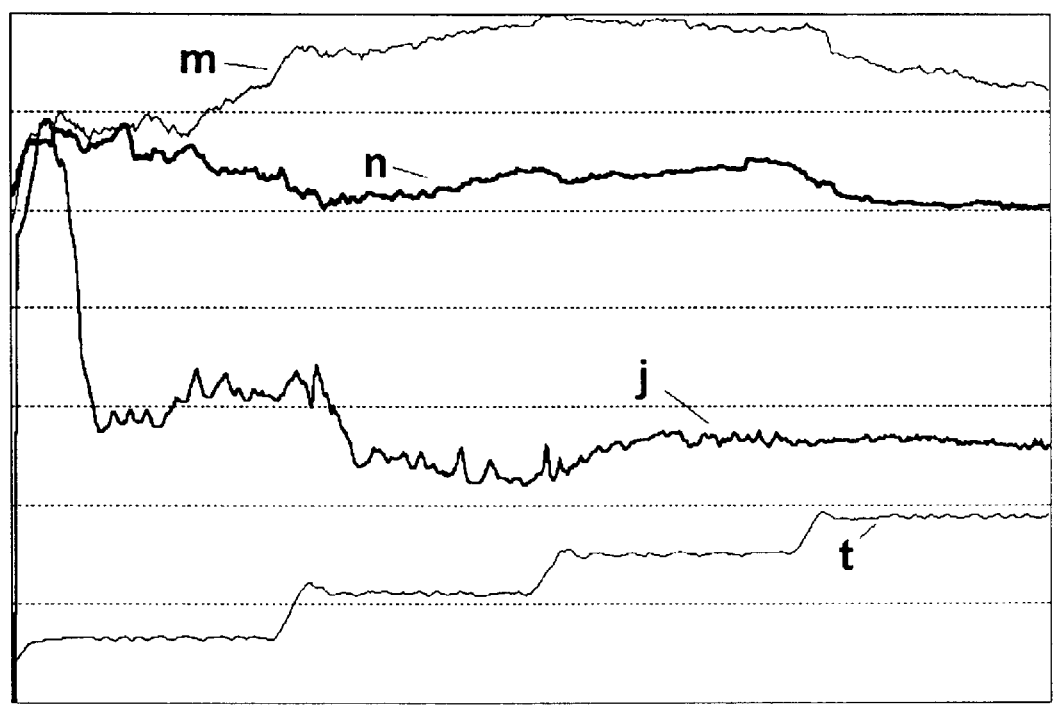
FIG. 5 show the friction traces for a dinuclear Mo complex, $Mo_2O_2S_2(coco_2dtc)_2$ tested at 75 ppm Mo concentration in oils 1 (no anti-oxidants) and 4 (with both bis-nonyldiphenylamine and Cu-PIBSA), and the friction trace for 75 ppm Mo as $Mo_3S_7((coco)_2dtc)_4$ in oil 4.

For comparison purposes a dinuclear molybdenum compound will be represented by $Mo_2O_2S_2(coco_2dtc)_2$ (MV822 from Vanderbilt) was also tested at 75 ppm Mo concentration in the Case 1 (no antioxidants) and Case 4 (with both DPA and Cu-PIBSA) oils. The function traces are shown in FIG. 5 along with that for 75 ppm Mo as $Mo_3S_7((coco)_2dtc)_4$ in the Case 4 oil.

With respect to the Figures:
For FIG. 1: Average Friction plot y axis 0 to 0.13
Samples are identified as
  a No ZDDP Base Case Oil
  b No ZDDP Base Case Oil +Antioxidants
  c $Mo_2O_2S_2(coco_2dtc)_2$
  d $Mo_2O_2S_2(coco_2dtc)_2$+Antioxidants
  e $Mo_2O_2S_2(2-eh_2dtc)_2$
  f $Mo_2O_2S_2(2-eh_2dtc)_2$+Antioxidants
  g $Mo_3S_4(2-eh_2dtc)_4$
  h $Mo_3S_4(2-eh_2dtc)_4$+Antioxidants
  i $Mo_3S_7(coco_2dtc)_4$
  j $Mo_3S_7(coco_2dtc)_4$+Antioxidants
  k $Mo_2O_2S_2(2-eh_2ddp)_2$
  l $Mo_2O_2S_2(2-eh_2ddp)_2$+Antioxidants
  m $Mo_2O_2S_2(hexyl_2ddp)_2$
  n $Mo_2O_2S_2(hexyl_2ddp)_2$+Antioxidants
  o $Mo_2O_2S_2(2-eh_2ddp)_2$
  p $Mo_2O_2S_2(2-eh_2ddp)_2$+Antioxidants
  q $Mo_3S_4(octyl_2ddp)_4$
  r $Mo_3S_4(octyl_2ddp)_4$+Antioxidants
  s $Mo_3S_7(lauryl_2ddp)_4$
  t $Mo_3S_7(lauryl_2ddp)_4$+Antioxidants
For FIGS. 2, 3 (Example 3) and 4, 5 (Example 4):
  For all plots:
  y axis=friction coefficient from 0 to 0.14
  secondary y axis for temperature=degrees C from 0 to 500
  x axis=time from 0 to 2 hours
  Samples are identified as:
  a Fresh oil
  b Fresh oil
  c 150 ppm Mo as $Mo_3S_4(2-eh_2dtc)_4$
  d 150 ppm Mo as $Mo_3S_4(2-eh_2dtc)_4$/DPA
  e 150 ppm Mo as $Mo_3S_4(2-eh_2dtc)_4$/CuPIBSA
  f 150 ppm Mo as $Mo_3S_4(2-eh_2dtc)_4$
  e 75 ppm Mo as $Mo_3S_7(coco_2dtc)_4$
  h 75 ppm Mo as $Mo_3S_7(coco_2dtc)_4$/DPA
  i 75 ppm Mo as $Mo_3S_7(coco_2dtc)_4$/CuPIBSA
  h 75 ppm Mo as $Mo_3S_7(coco_2dtc)_4$
  k 150 ppm Mo as $Mo_2O_2S_2(coco_2dtc)_2$
  l 150 ppm Mo as $Mo_2O_2S_2(coco_2dtc)_2$
  m 75 ppm Mo as $Mo_2O_2S_2(coco_2dtc)_2$
  n 75 ppm Mo as $Mo_2O_2S_2(coco_2dtc)_2$
  t representative temperature profile

What is claimed is:

1. A lubricating oil composition comprising an admixture of a major amount of an oil of lubricating viscosity and a minor amount of at least one compound comprising a trinuclear molybdenum core having bonded thereto ligands capable of rendering the compound oil soluble and at least one antioxidant, said compound comprising a trinuclear molybdenum core being present in an amount sufficient to provide said composition with at least 1 ppm of molybdenum.

2. The composition of claim 1 wherein the core contains at least trinuclear molybdenum and sulfur.

3. The composition of claim 1 wherein the core consists of trinuclear molybdenum and sulfur.

4. The composition of claim 1 wherein the antioxidant is selected from the group consisting of copper-containing antioxidants, sulfur-containing antioxidants, phenolic antioxidants and aromatic amine containing antioxidants and mixtures thereof.

5. The composition of claim 1 wherein the antioxidant is a copper containing compound selected from the group consisting of copper carboxylates, copper dialkyldithiophosphates and copper dialkyldithiocarbamates.

6. The composition of claim 1 wherein the antioxidant is at least one selected diphenylamine and diphenylamine derivatives.

7. The composition of claim 1 wherein the antioxidant is a mixture of copper-containing antioxidants in combination with at least one of diphenylamine and diphenylamine derivatives.

8. The composition of claim 1 wherein the antioxidant is a copper containing antioxidant and the amount of copper is from 1 ppm to 1000 ppm of copper in the oil.

9. The composition of claim 1 wherein the antioxidant is a copper containing antioxidant and the amount of copper is from 1 ppm to 200 ppm copper in the oil.

10. The composition of claim 1 wherein the antioxidant is an aromatic amine containing antioxidant.

11. The composition of claim 10 wherein the aromatic amine is present in an amount of up to 2 wt % based on the weight of the oil.

12. The composition of claim 1 wherein the amount of molybdenum from the trinuclear molybdenum compound is present in an effective amount of from 1 to 2000 ppm in the finished oil.

13. The composition of claim 1 wherein the amount of molybdenum from the trinuclear molybdenum compound is an effective amount of from about 5 to 750 ppm in finished oil.

14. The composition of claim 1 wherein the molybdenum is in the +4 oxidation state.

15. The composition of claim 1 wherein the oil is substantially free of sulfur.

16. The composition of claim 1 further comprising at least one of dispersants, detergents, pour point depressants, viscosity modifiers, surfactants and antiwear agents.

17. A lubricating oil composition comprising an admixture of a major amount of an oil of lubricating viscosity, a minor amount of at least one antioxidant and at least one trinuclear molybdenum compound having the formula $Mo_3S_kL_nQ_z$, and mixtures thereof in an amount sufficient to provide said composition with at least 1 ppm of molybdenum, wherein L are independently selected ligands containing hydrogen and hydrocarbyl groups sufficient to render the compound oil soluble, n is 1 to 4, k is 4 through 10, Q is an electron donating compound and z is 0 to 5.

18. The composition of claim 17 wherein the neutral electron donating compound is selected from the group consisting of water, amines, alcohols, phosphines, and ethers.

19. The composition of claim 17 wherein the ligands, L, are represented by at least one structure having the formula:

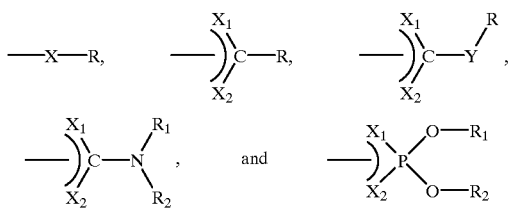

and perthio derivatives thereof, wherein X, $X_1$, $X_2$, and Y are selected from oxygen and sulfur and wherein $R_1$, $R_2$, and R are independently selected from the group consisting of hydrogen and organo groups.

20. The composition of claim 19 wherein the organo groups are independently selected from alkyl, aryl, substituted aryl, and ether groups.

21. The composition of claim 20 wherein the trinuclear molybdenum compounds have a total of at least 21 carbon atoms among all the ligands' organo groups.

22. The composition of claim 19 wherein the organo groups are alkyl groups and the number of carbon atoms in each alkyl group ranges from about 1 to 100.

23. The composition of claim 20 wherein the number of carbon atoms in each of the alkyl groups ranges from about 1 to about 30.

24. The composition of claim 19 wherein the ligands, L, are independently selected from dialkyldithiophosphates, thioxanthates, dialkyldithiocarbamates, and xanthates.

25. A lubricating oil composition comprising an admixture of a major amount of an oil of lubricating viscosity, a minor amount of at least one antioxidant and at least one trinuclear molybdenum compound having the formula $Mo_3S_kE_xL_nQ_z$ and mixtures thereof in an amount sufficient to provide said composition with at least 1 ppm of molybdenum, wherein k is at least 1, E is selected from the group consisting of oxygen and selenium, x is at least one, the sum of k and x is at least 4 and L are independently selected ligands containing hydrogen and hydrocarbyl groups sufficient to render the compound oil soluble, n is from 1 to 4, Q is a neutral electron donating compound and z is from 0 to 5.

26. A concentrate for blending with a lubricating oil comprising: an oleagenous carrier and from about 1 to about 90 wt % based on the weight of the concentrate of a mixture of at least one antioxidant and at least one trinuclear molybdenum compound in an amount sufficient to provide the lubricating oil with at least 1 ppm of molybdenum.

27. The concentrate of claim 26 wherein the trinuclear compound is represented by the formula $MO_3S_kL_nQ_z$, and mixtures thereof, wherein L are independently selected ligands, n is from 1 to 4, k varies from 4 through 10, Q is a neutral electronic donating compound, and z ranges from 0 to 5.

28. The concentrate of claim 26 wherein the antioxidant is selected from the group consisting of copper-containing antioxidants and aromatic amine-containing antioxidants and mixtures thereof.

29. A lubricating oil composition comprising: a major amount of an oil of lubricating viscosity to which is added a minor amount of at least one trinuclear molybdenum compound sufficient to provide said composition with at least 1 ppm of molybdenum and a minor amount of at least one antioxidant.

30. A method for making a lubricating oil composition comprising: combining an oil of lubricating viscosity, at least one antioxidant and an amount of at least one trinuclear molybdenum compound sufficient to provide said composition with at least 1 ppm of molybdenum.

31. The product of claim 30.

32. The method of claim 30 wherein the antioxidant is selected from the group consisting of copper-containing antioxidants, aromatic amine-containing antioxidants, and mixtures thereof.

33. The method of claim 30 wherein the antioxidant is a copper-containing antioxidant.

34. A method for lubricating an internal combustion engine comprising:

treating moving parts of an internal combustion engine with an oil of lubricating viscosity containing at least one trinuclear molybdenum compound in an amount sufficient to provide said oil with at least 1 ppm of molybdenum, and at least one antioxidant.

* * * * *